United States Patent
Wenger et al.

(10) Patent No.: US 7,855,059 B2
(45) Date of Patent: Dec. 21, 2010

(54) FERMENTATION WITH CYCLIC PULSE-PAUSE FEEDING

(75) Inventors: Kevin S. Wenger, Wake Forest, NC (US); Maria Antonieta Caicedo, Wake Forest, NC (US); Stuart Michael Stocks, Bagsvaerd (DK); Swapnil Bhargava, Baltimore, MD (US); Mark R. Marten, Eldersberg, MD (US)

(73) Assignee: Novozymes A/S, Bagsvaerd (DK)

( * ) Notice: Subject to any disclaimer, the term of this patent is extended or adjusted under 35 U.S.C. 154(b) by 386 days.

(21) Appl. No.: 10/490,565

(22) PCT Filed: Jun. 4, 2002

(86) PCT No.: PCT/DK02/00377
§ 371 (c)(1), (2), (4) Date: Mar. 18, 2004

(87) PCT Pub. No.: WO03/029439
PCT Pub. Date: Apr. 10, 2003

(65) Prior Publication Data
US 2005/0064536 A1 Mar. 24, 2005

Related U.S. Application Data

(60) Provisional application No. 60/326,611, filed on Oct. 1, 2001.

(51) Int. Cl.
*C12P 1/00* (2006.01)

(52) U.S. Cl. ............ 435/71.1; 435/71.2; 435/71.3; 435/171; 435/170

(58) Field of Classification Search ............ 435/41, 435/71.1, 71.2, 71.3, 170, 886, 171, 913; 71/8
See application file for complete search history.

(56) References Cited

U.S. PATENT DOCUMENTS 4,468,455 A * 8/1984 Hopkins .......... 435/3

FOREIGN PATENT DOCUMENTS

| CA | 1292962 | * 12/1991 |
| WO | WO 01/20016 | 3/2001 |

OTHER PUBLICATIONS

Li et al., Biotechnology and Bioengineering, vol. 70, No. 3, p. 300-312, (Nov. 5, 2000).
Abstract No. XP-002181125, 1999: 144152 Caplus.
Abstract No. XP-008009695, 1993.
Abstract No. XP-001030780, Biotechnology Letters, vol. 9, No. 9, pp. 617-620 (1987).
Lin et al., Journal of Biotechnology, vol. 79, pp. 27-37, (2000).

* cited by examiner

*Primary Examiner*—Allison M Ford
(74) *Attorney, Agent, or Firm*—Michael W. Krenicky

(57) ABSTRACT

A process for the production of a valuable compound, comprising the steps of a) fermentation of a filamentous bacterial or fungal strain (e.g. a *Streptomyces* strain or an *Aspergillus* strain) in a fermentation medium wherein a carbohydrate during fermentation is added in a cyclic pulse dosing/pause way, wherein the pulse dosing time is shorter than the pause time and b) recovery of the valuable compound from the fermentation broth.

21 Claims, 1 Drawing Sheet

FERMENTATION WITH CYCLIC PULSE-PAUSE FEEDING

CROSS-REFERENCE TO RELATED APPLICATIONS

This application is a 35 U.S.C. 371 national application of PCT/DK2002/000377 filed Jun. 4, 2002, which claims the benefit under 35 U.S.C. 119 of U.S. provisional application No. 60/326,611 filed Oct. 1, 2001, the contents of which are fully incorporated herein by reference.

TECHNICAL FIELD

The present invention relates to a method of reducing broth viscosity during fermentation.

BACKGROUND ART

Filamentous microorganisms are one of the workhorses for industrial microbiology, as they are used for the commercial production of many different therapeutics (e.g. penicillin and cephalosporin), commodity chemicals (e.g. citric acid) and commercial enzymes (e.g. proteases and amylases).

It has been known for decades that fermentations of filamentous microorganisms present unique engineering challenges. Specifically, the mycelial morphology of filamentous microorganisms often leads to high viscosities which reduce the ability to agitate, pump, and supply oxygen to these broths.

Despite extensive study, there has been relatively little success in altering the morphology to reduce broth viscosity in industrial-scale systems. In fact, the most common approaches to reduce the broth viscosity have been to add water to dilute the broth or to increase agitation to fragment the mycelia. Neither of these methods has proven to be consistently effective.

SUMMARY OF THE INVENTION

The inventors have found that broth viscosity may be altered in a beneficial way by adjusting the carbon feed profile during fermentation so we claim:

A process for the production of a valuable compound, comprising the steps of:

a) fermentation of a filamentous bacterial or fungal strain in a fermentation medium wherein a carbohydrate during fermentation is added in a cyclic pulse dosing/pause way, wherein the pulse dosing time is shorter than the pause time; and b) recovery of the valuable compound from the fermentation broth.

BRIEF DESCRIPTION OF DRAWING

The present invention is further illustrated by reference to the accompanying drawing, in which.

DETAILED DISCLOSURE OF THE INVENTION

Figure 1:
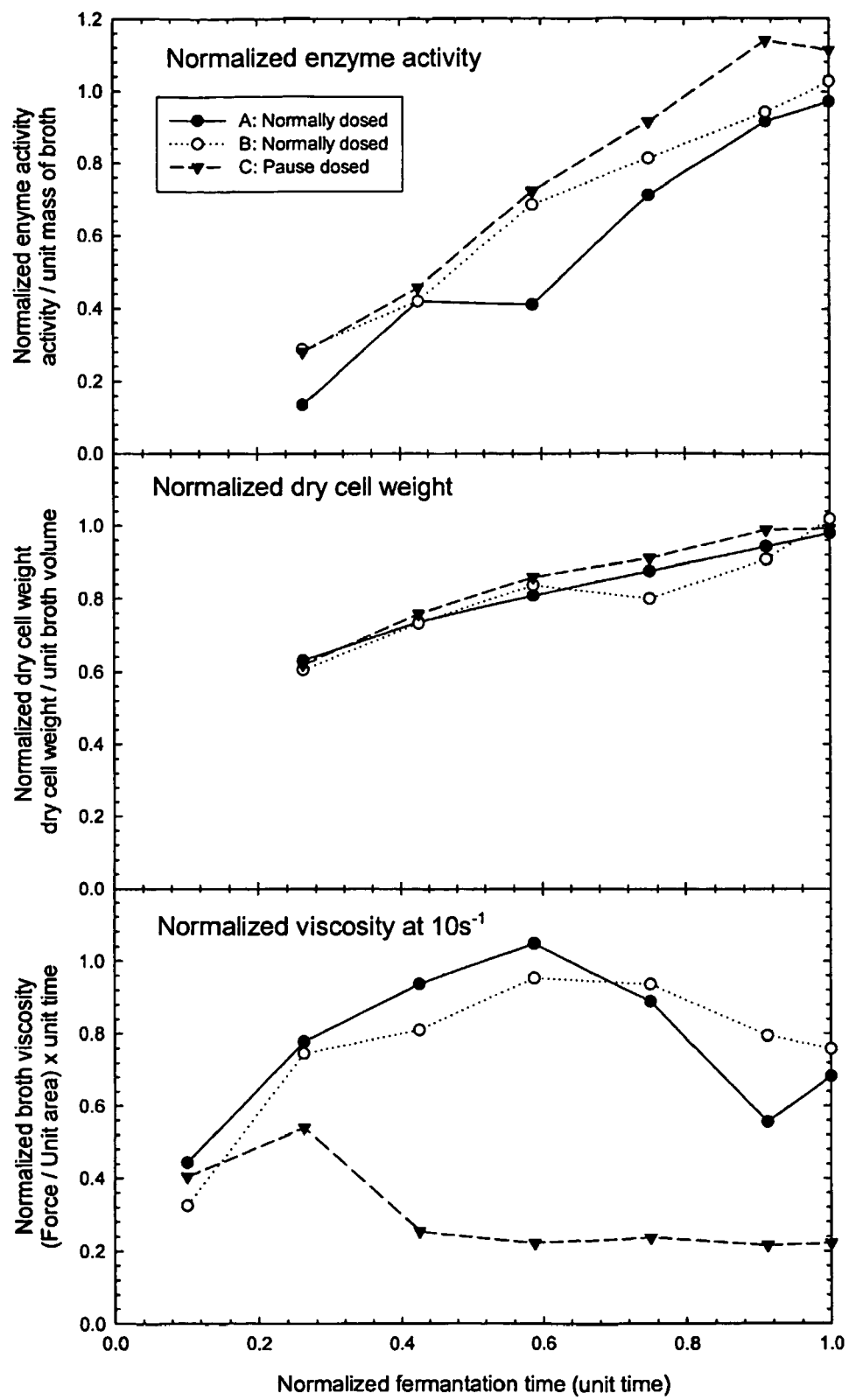
FIG. 1 shows the enzyme activity, the dry cell weight and the broth viscosity (in a normalized form) from 3 fed batch fermentations of a *Streptomyces* strain (see Example 2). The only difference between the fermentations is that one of them has a prolonged pause time.

The inventors have shown that cyclic feeding of cells during fed-batch fermentation may be used as a means to reduce broth viscosity. During the fermentations, glucose was fed either continuously, or in repeated 300 sec cycles, with the feed pump on for either 30 or 150 sec during each cycle. In all fermentations, cultures were fed the same total amount of glucose (see Example 1).

Data indicate that pulsed feeding has no significant effect on time profiles for total dry cell weight, oxygen mass transfer rate, or total base added during the course of each fermentation (variables indicative of cellular metabolic activity). In addition, pulsed feeding appears to have no measurable effect on total extracellular protein concentration or the apparent distribution of extracellular proteins.

In contrast, pulsed feeding has a significant effect on morphology. Cells fed in pulses were smaller than cells fed continuously. As a result, viscosity is lower in pulse-fed fermentations than in fermentations fed continuously.

Valuable Compounds

The valuable compound according to the invention may be an antibiotic such as penicillin or cephalosporin or erythromycin, or a commodity chemical such as citric acid. The valuable compound may also be a therapeutic protein such as insulin or an enzyme (e.g. a hydrolase, a transferase, a lyase, an isomerase, or a ligase, in particular a carbohydrolase, a cellulase, an oxidoreductase, a protease, an amylase, a lipase, or a carbohydrase).

Microbial Strains

The microbial strain according to the invention may be obtained from any filamentous bacterial or fungal strain of any genus.

For example, in a preferred embodiment the valuable compound may be obtained from a *Streptomyces* strain, e.g., a *Streptomyces lividans* strain or *Streptomyces murinus* strain or from an *Actinomyces* strain.

In another preferred embodiment the valuable compound may be obtained from a filamentous fungal strain such as an *Acremonium, Aspergillus, Aureobasidium, Cryptococcus, Filibasidium, Fusarnum, Humicola, Magnaporthe, Mucor, Myceliophthora, Neocallimastix, Neurospora, Paecilomyces, Penicillium, Piromyces, Schizophyllum, Talaromyces, Thernoascus, Thielavia, Tolypocladium,* or *Trichoderma* strain, in particular the valuable compound may be obtained from an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma iongibrachiatum, Trichoderma reesei,* or *Trichoderma viride* strain.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

For purposes of the present invention, the term "obtained from" as used herein in connection with a given source shall mean that the valuable compound is produced by the source or by a cell in which a gene from the source has been inserted.

Fermentations

The microbial strain may be fermented by any method known in the art. The fermentation medium may be a complex medium comprising complex nitrogen and/or carbon sources, such as soybean meal, cotton seed meal, corn steep liquor, yeast extract, casein hydrolysate, molasses, and the like. The fermentation medium may be a chemically defined media, e.g. as defined in WO 98/37179.

The fermentation may be performed as a fed-batch, a repeated fed-batch or a continuous fermentation process.

In a fed-batch process, either none or some of the compounds comprising one or more of the structural and/or catalytic elements are added to the medium before the start of the fermentation and either all or the remaining part, respectively, of the compounds comprising one or more of the structural and/or catalytic elements is fed during the fermentation process. The compounds which are selected for feeding can be fed together or separate from each other to the fermentation process.

In a repeated fed-batch or a continuous fermentation process, the complete start medium is additionally fed during fermentation. The start medium can be fed together with or separate from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth.

In a preferred embodiment of the invention, a fed-batch or a repeated fed-batch process is applied.

Carbohydrates

Any carbohydrate as defined in Morrison and Boyd: Organic Chemistry, p. 1056, 4$^{th}$ edition: "Carbohydrates are polyhydroxy aldehydes, polyhydroxy ketones, or compounds that can be hydrolysed to them. A carbohydrate that cannot be hydrolysed to simpler compounds is called a monosaccharide. A carbohydrate that can be hydrolysed to two monosaccharide molecules is called a disaccharide. A carbohydrate that can be hydrolysed to many monosaccharides is called a polysaccharide", may be used according to the invention.

A carbohydrate selected from the group consisting of glucose, sucrose, glucose syrup, fructose, maltose, lactose, trehalose, oligosaccharides, limit dextrins, dextrins, hydrolysed corn dextrin, starch, cyclodextrins, maltulose, mannose, and galactose, is preferred; in particular a carbohydrate from the group consisting of glucose, sucrose, maltose and hydrolysed dextrin, is preferred.

According to the invention the carbohydrate will normally be added in an amount of from 0.01 g carbohydrate/kg broth/hr to 10 g carbohydrate/kg broth/hr; in particular in an amount of from 0.1 g carbohydrate/kg broth/hr to 5 g carbohydrate/kg broth/hr; in a most preferred embodiment of from 0.5 g carbohydrate/kg broth/hr to 2 g carbohydrate/kg broth/hr.

Cyclic Pulse Dosing/Pause

According to the invention the carbohydrate during fermentation is added in a cyclic pulse dosing/pause way. By "pulsing" the carbohydrate and "pausing" the carbohydrate a "controlled" starvation occurs, and the viscosity is reduced. The overall average feed rate is maintained by increasing the amount of carbohydrate dosed during the pulse time, according to the ratio of the pulse/pause times.

In a preferred embodiment the carbohydrate pulse dosing is lasting of from 10 sec. to 1000 sec.; in particular of from 1 sec. to 500 sec.; preferably of from 5 sec. to 100 sec.

In a preferred embodiment the pause is lasting of from 60 sec. to 1800 sec. (1 min. to 30 min.); preferably of from 300 sec. to 1800 sec. (5 min. to 30 min.).

According to the present invention the pulse dosing time is shorter than the pause time, e.g. the pulse dosing time may be lasting 30 sec. and the pause time may be lasting e.g. 300 sec.

Recovery of the Valuable Compound

A further aspect of the invention concerns the downstream processing of the fermentation broth. After the fermentation process is ended, the valuable compound may be recovered from the fermentation broth, using standard technology developed for the valuable compound of interest. The relevant downstream processing technology to be applied depends on the nature and the cellular localization of the valuable product. First the valuable compound is separated from the fermentation fluid using e.g. centrifugation or filtration. The valuable compound is recovered from the biomass, in case that the valuable product is accumulated inside or associated with the microbial cells. Otherwise, when the valuable product is excreted from the microbial cell, it is recovered from the fermentation fluid as known in the art.

The invention is further illustrated in the following examples which are not intended to be in any way limiting to the scope of the invention as claimed.

Example 1

Materials and Methods

Strain and Growth Conditions

In all experiments *Aspergillus oryzae* was used (derived from strain IFO 4177, institute for fermentation, Osaka, Japan).

For storage, freeze-dried spores were suspended with 0.1% Tween 80 solution and glycerol was added to a final concentration of 30% (w/v). The spore suspension was maintained at −70° C. For inoculation, frozen spores were germinated on fresh agarose slants (yeast extract 4.0 g/l, Dextrose monohydrate 5.0 g/l, Potassium phosphate monobasic 1.0 g/l, Magnesium sulfate 0.5 g/l, agar 10 g/l), allowed to sporulate, and used to inoculate seed fermentors (20 L).

In all seed cultures, 8 L of a complex growth medium was used with the following composition: Glucose 20.0 g/l, $(NH_4)_2SO_4$ 2.5 g/l, Yeast extract 10.0 g/l, $KH_2PO_4$ 1.5 g/l, NaCl 1.0 g/l, $MgSO_4.7H_2O$ 1.0 g/l, $CaCl_2.2H_2O$ 0.10 g/l. After sterilization, 1.0 ml of a filter sterile trace mineral solution ($ZnSO_4.7H_2O$ 5.7 g/l, $CuSO_4.5H_2O$ 1.0 g/l, $NiCl_2.6H_2O$ 0.2 g/l, $FeSO_4.7H_2O$ 5.5 g/l, $MnSO_4.H_2O$ 3.4 g/l) was added. Medium pH was then adjusted to 3.3 using KOH or $H_3PO_4$. During seed fermentations, temperature was maintained at 30° C., air flow rate was controlled at 1.0 VVM, impeller speed was controlled at 750 rpm, and pH was maintained at 3.3 by addition of $NH_3$. Seed culture was grown until oxygen uptake rate for the cells reached an arbitrary value of 0.3 mmol/(liter×min), at which time 5% (v/v) seed culture was used to inoculate experimental fermentations.

Fermentation Conditions

Fermentors with a nominal volume of 20 liters and a working volume of 13 liters were used. Growth medium contained: Glucose 5.0 g/l, $(NH_4)_2SO_4$ 2.5 g/l, $KH_2PO_4$ 3.75 g/l, NaCl 2.5 g/l, $MgSO_4.7H_2O$ 2.5 g/l, $CaCl_2.2H_2O$ 0.25 g/l. After sterilization, 17.5 mL filter sterile trace mineral solution (described above) was added. For all runs, pH was maintained at 6.0 using NH3, temperature was maintained at 30° C., air flow rate was controlled at 1.0 VVM, and impeller speed was controlled at 750 rpm. In control fermentations, a glucose solution (65% w/v) was fed continuously at a rate of 10 g glucose per hr, after a 10% rise in the dissolved oxygen level during the initial batch mode. Other fermentations were fed as described in the text. Samples were taken at regular intervals and analyzed for biomass using duplicate measurements of dry cell mass. Morphology and rheological properties were determined as described below.

Morphology

Images of fungal elements, which included both freely dispersed mycelium and clumps, were analyzed in order to quantify morphology. Samples for image analysis were prepared by mixing 1 ml of broth with equal volume of fixative solution (Paul, G C and Thomas, C R (1998) Characterization of Mycelial Morphology Using Image Analysis. Adv. Biochem. Eng. 60: 1-59) and stored at 4° C. for later analysis. For image analysis, fixed samples were diluted with 20% sucrose solution to a final concentration of 0.2 g/l to prevent artifacts from cell overlap. Images were captured using a CCD video camera (Sony) mounted on an inverted stage phase contrast microscope (IMT-2, Olympus) and digitized by a frame grabber card (G-3, Scion) installed on a Macintosh computer (Quadra 950). Image analysis was done using NIH Image V1.6 downloaded from Internet at http://rsb.info.nih.gov/nih-image/. Clumps and freely dispersed mycelium were measured together using average projected area. Since mycelia have approximately constant hyphal width, projected area is a close measure of volume and thus can be used to quantify biomass. For each sample, images of at least 100 fungal elements were analyzed to determine average projected area for that sample.

Rheological Analysis

All rheological tests were performed using a rotational viscometer (DVII+, Brookfield) with a "vane and cup" geometry. The vane and cup system, its calibration, and the rheological testing procedure used have been described previously (Marten, M R, Wenger, K S and Khan, S A (1997). Rheology, Mixing Time, and Regime Analysis for a Production-Scale *Aspergillus oryzae* Fermentation. Bioreactor and Bioprocess Fluid Dynamics. A. W. Nienow. Ednburgh, BHR Group, Cranfield, UK: 295-313). The Herschel-Bulkley equation ($\tau=\tau_y+K\gamma^n$) was used to describe rheological character of all batches, and apparent viscosity ($\kappa$) is calculated as ($\tau_{avg}/\gamma_{avg}$), with ave rage shear stress and shear rate determined as described in Marten, M R, Wenger, K S and Khan, S A (1997). Rheology, Mixing Time, and Regime Analysis for a Production-Scale *Aspergillus oryzae* Fermentation. Bioreactor and Bioprocess Fluid Dynamics. A. W. Nienow. Ednburgh, BHR Group, Cranfield, UK: 295-313.

Statistical Data Analysis

Analysis of variance (ANOVA) was preformed for statistical comparisons. Significance level ($\alpha$) was chosen to be 0.05. Thus, a P-value or significance probability (P) less than 0.05 is considered an indication (95% confidence) of a significant difference between groups. Tolerances on average values are reported as standard error on the mean.

Gel Electrophoresis

To determine the distribution of the proteins secreted in the extra-cellular medium, SDS-polyacrylamide gels (12% homogeneous, Bio-Rad) were used.

Samples were prepared in Laemmli buffer with β-mercaptoethanol, and were heated before loading equal volumes. To determine the molecular weight of proteins, low-range molecular weight standard proteins (Bio-Rad) were used. To quantify protein bands, gels were scanned (GS-800, Bio-Rad) and bands were analyzed (Quantity One software, Bio-Rad) by calculating the trace quantity (i.e. quantity of a band as measured by the area under its peak profile).

Results

A series of nine fed-batch fermentations at three different "pulse fraction" (PF) values were conducted:

Pulse Fraction (PF)=(Feed–Pump "On" Time)/(Total Cycle Time).

In all the fermentations total cycle time was 300 sec. As a control, three fed-batch fermentations were carried out with PF=1.0, and a constant glucose feed rate of 10 g/hr. A second set of three fermentations was carried out with PF=0.5, and glucose addition rate of 20 g/hr, and a third set of three fermentations was conducted with PF=0.1, and glucose feed rate of 100 g/hr. With this arrangement, the same total amount of glucose was added in all fermentations, regardless of the PF value, during each five minute cycle. Initial glucose concentration during all fermentations was 5 g/l, and feeding started after a 10% rise in dissolved oxygen. On-line measurements were made for oxygen uptake rate (OUR), carbon dioxide evolution rate (CER), total base added, and samples were taken for off-line analysis of fungal morphology, broth rheology and biomass concentration.

Fungal biomass, measured as dry cell weight, increases approximately linearly over the course of all fermentations to a final value of approximately 17 g/l. A regression analysis showed no significant difference (95% confidence) between biomass profiles for fermentations at the three different PF values.

Total base added for pH control rised approximately linearly for all batches with no discernable difference for the three PF values. Thus, pulsed feeding during fed-batch operation has no apparent effect on these variables, indicative of cellular metabolic activity.

Total extra-cellular protein concentration as a function of time during the same nine fermentations showed that the initial protein concentration of approximately 1 g/l, due to carry-over of protein from the inoculum, failed during the batch portion of the fermentation. After initial glucose was consumed, feeding begins and low residual glucose levels allow expression of secreted proteins. This leads to the apparently linear rise in total protein concentration that continues until the end of each batch. A regression analysis showed no significant difference (95% confidence) between protein concentration profiles for fermentations at the three different PF values.

Extra-cellular protein concentration (g extra-cellular protein per g dry cell mass) during the fed-batch portion of the fermentations showed average values of 0.11±0.003, 0.11±0.005 and 0.10±0.005 for PF values of 1.0, 0.5 and 0.1 respectively, with no significant difference between these values. Thus, it appears that pulsed feeding has no observable effect on total extra-cellular protein concentration profiles.

In addition to total extra-cellular protein, we used SDS-PAGE to follow the apparent distribution of these proteins as a function of time. The relative concentration of six of these proteins was determined, and regression analysis showed no significant difference in the apparent distribution of proteins between fermentations operated at the different PF values. Thus, pulsed feeding does not appear to have changed the expression pattern or apparent distribution of extracellular proteins in this system.

While pulse feeding had no observable effect on metabolic variables or extra-cellular protein expression, it had a measurable effect on fungal morphology, in particular, the average size of fungal elements. To measure the size of fungal elements we use average projected area (A), which takes into account both freely dispersed mycelia and clumps (no pellets were found in any fermentations described here). The average projected area can be divided into three distinct time periods. During the first period or batch portion of each fermentation (t<18 hr), A rises as a function of time. During the second period (18<t<50 hr), initial glucose is exhausted, feeding has begun, and A begins to decrease. This continues until the third period (50<t<110 hr), where A remains at an approximately constant value. Regression analysis shows no significant difference between A profiles during these first two periods. In contrast, between 50 hours and the end of the each batch, there is a significant difference in time averaged A between fermentations with PF=1.0 and 0.5 (P=2.2×10−4), and between fermentations with PF=1.0 and 0.1 (P=7.4×10−5).

Thus, pulsed feeding had a measurable and significant effect on fungal morphology. Fungal elements in pulsed fermentations were smaller than those fed a continuous stream of glucose. Morphological behavior during these fermentations appears to have had a measurable effect on broth viscosity. We found that just as with morphology, behavior of broth viscosity can be divided into three distinct time periods. During the first period (t<18 hr) viscosity rose as a function of time, during the second period (180<t<50 hr) viscosity remained relatively constant, and during the third period (t>50 hr) viscosity rose again.

During the first time period or batch phase, both biomass and A were increasing, and as a result viscosity also increased. During the second period, biomass continued to increase, but A was decreasing. Apparently, these two phenomena off-set each other, and as a result viscosity remained relatively constant. During the third time period, biomass rose while A remained constant, leading to a second rise in viscosity. Statistical analysis of time averaged viscosity during the first two periods (t<50 hr) showed no significant difference for fermentations operated at the three different PF values. However, during the third period (t>50 hr) viscosity in pulse-fed fermentations was significantly lower than viscosity in control fermentations. We found that the time averaged values of viscosity during this period were 0.47±0.073, 0.23±0.022, and 0.17±0.019 for fermentations operated at PF values of 1.0, 0.5, and 0.1 respectively, with a statistically significant difference between fermentations operated at PF=1.0 and 0.5 (P=1.8×10$^{-5}$), and between fermentations operated at PF=1.0 and 0.1 (P=2.4×10$^{-6}$).

It appears that a simple feeding strategy, in particular wherein the pulse dosing time is shorter than the pause time, can be used to produce smaller fungal mycelia, leading to a significant reduction in fermentation broth viscosity.

Example 2

*Streptomyces* Fermentation

The second example of a beneficial reduction in broth viscosity comes from the filamentous bacterium *Streptomyces murinus*, producing a native intracellular protein. Prolonging the pause time increases productivity slightly and significantly reduces the broth viscosity.

Method

Three identical pilot scale fermenters were seeded from the same seed tank and ran simultaneously with a start weight of 250 kg for equal lengths of time. The seed medium was formulated from common fermentation ingredients including glucose, corn-steep liquor, potassium phosphate and ammonium sulphate. The main tank medium was similarly formulated and also included sodium phosphate, magnesium sulphate and some trace metals. After an initial period of growth in the main tank, a glucose feed was started and the rate held constant for the rest of the fermentation. I.e. the fermentation was typical of a fermentation process for this sort of organism.

Measurements of Enzyme activity per unit weight of culture broth, and dry cell weight per unit volume of culture broth were measured by validated methods conforming with ISO 9001. Viscosity was measured in a Carrimed controlled stress rheometer with a 6 cm cone and plate geometry. The instrument was instructed to apply a shear rate of 10 s$^{-1}$ & 100 s$^{-1}$ and the steady state stress used to calculate the apparent viscosity.

Results

FIG. 1 shows the results (in a normalized form) from the three fed batch fermentations. The only difference between the fermentations is that the last of the three ran with a prolonged pause time: The pulse dosing time was as fast as possible (<10 sec.), and the pause time was 7 min.

The activity per unit mass data shows a small but positive effect on the enzyme activity from pulse-paused dosing. The cell dry weight per unit volume data shows no effect from pulse-paused dosing. The viscosity data shows a dramatic and highly beneficial reduction in broth viscosity upon for pulse paused dosing.

CONCLUSION

Pulse-Paused dosing results in a small increase in productivity and a dramatic reduction of viscosity. This has a major impact on mixing performance at the large scale and will lead to the opportunity of running large scale fermentations to a higher biomass concentration and therefore a higher productivity.

The invention claimed is:

1. A process for producing a compound, comprising the steps of:
   (a) fermenting a filamentous bacterial or fungal strain in a fermentation medium wherein a carbohydrate is added during fermentation to the fermentation medium by a cyclic pulse dosing/pause method, wherein the cyclic pulse dosing/pause method comprises alternating between (i) dosing the fermentation medium with the carbohydrate for a pulse feeding period of from 1 to 1000 seconds and (ii) a pausing period of from 60 to 1800 seconds without dosing the carbohydrate, wherein the carbohydrate is feed for the filamentous bacterial or fungal strain; and
   (b) recovering the compound from the fermentation medium;
   wherein the compound is an antibiotic or a protein.

2. The process of claim 1, wherein the compound is an antibiotic.

3. The process of claim 1, wherein the compound is a protein.

4. The process of claim 3, wherein the protein is an enzyme.

5. The process of claim 4, wherein the enzyme is a hydrolase, oxidoreductase, isomerase, ligase, lyase, or transferase.

6. The process of claim 5, wherein the enzyme is an amylase, carbohydrase, cellulase, lipase, or protease.

7. The process of claim 1, wherein the fermentation is with a filamentous bacterial strain.

8. The process of claim 7, wherein the filamentous bacterial strain is an *Actinomyces* or *Streptomyces* strain.

9. The process of claim 1, wherein the fermentation is with a filamentous fungal strain.

10. The process of claim 9, wherein the filamentous fungal strain is an *Aspergillus* strain.

11. The process of claim 10, wherein the filamentous fungal strain is an *Aspergillus oryzae* strain.

12. The process of claim 1, wherein the carbohydrate is selected from the group consisting of glucose, sucrose, glucose syrup, fructose, maltose, lactose, trehalose, oligosaccharides, limit dextrins, dextrins, hydrolyzed dextrin, starch, cyclodextrins, maltulose, mannose, and galactose.

13. The process of claim 12, wherein the carbohydrate is selected from the group consisting of glucose, hydrolyzed dextrin, maltose, and sucrose.

14. The process of claim 1, wherein the carbohydrate is added in an amount of from 0.01 g carbohydrate/kg broth/hr to 10 g carbohydrate/kg broth/hr.

15. The process of claim 14, wherein the carbohydrate is added in an amount of from 0.1 g carbohydrate/kg broth/hr to 5 g carbohydrate/kg broth/hr.

16. The process of claim 15, wherein the carbohydrate is added in an amount of from 0.5 g carbohydrate/kg broth/hr to 2 g carbohydrate/kg broth/hr.

17. The process of claim 1, wherein the pulse feeding period is from 1 to 500 seconds and the pausing period is from 300 to 1800 seconds.

18. The process of claim 17, wherein the pulse feeding period is from 5 to 100 seconds.

19. The process of claim 17, wherein the fermentation is a fed-batch or a repeated fed-batch process.

20. The process of claim 1, wherein the pulse feeding period is shorter than the pausing period.

21. A process for producing a compound, comprising the steps of:
   (a) fermenting a filamentous bacterial or fungal strain in a fermentation medium wherein a carbohydrate is added during fermentation to the fermentation medium by a cyclic pulse dosing/pause method, wherein the cyclic pulse dosing/pause method comprises alternating between (i) dosing the fermentation medium with the carbohydrate for a pulse feeding period of from 1 to 500 seconds and (ii) a pausing period of from 60 to 1800 seconds without dosing the carbohydrate, wherein the carbohydrate is feed for the filamentous bacterial or fungal strain; and
   (b) recovering the compound from the fermentation medium;
   wherein the compound is an antibiotic or a protein.

* * * * *